United States Patent [19]

Steer et al.

[11] Patent Number: 4,460,363
[45] Date of Patent: Jul. 17, 1984

[54] OSTOMY BAG

[75] Inventors: Peter L. Steer; John V. Edwards, both of East Grinstead, England

[73] Assignee: Kingsdown Medical Consultants, Ltd., London, England

[21] Appl. No.: 394,659

[22] Filed: Jul. 2, 1982

Related U.S. Application Data

[63] Continuation of Ser. No. 881,274, Feb. 27, 1978, abandoned.

[51] Int. Cl.³ .............................................. A61F 5/44
[52] U.S. Cl. .................................... 604/336; 604/342; 604/344; 604/339
[58] Field of Search .............. 128/283; 150/8; 285/86, 285/304; 604/332, 337, 338, 339, 342, 336, 344

[56] References Cited

U.S. PATENT DOCUMENTS

| | | | |
|---|---|---|---|
| 214,991 | 1/1879 | Coler | 285/423 |
| 2,555,086 | 4/1951 | Guinn | 128/283 |
| 2,638,898 | 2/1953 | Perry | 128/283 |
| 2,639,710 | 5/1953 | Fazio | 128/283 |
| 2,720,332 | 3/1955 | Holt | 285/DIG. 22 |
| 2,721,553 | 1/1955 | Perry | 128/283 |
| 2,787,270 | 7/1957 | Perry | 128/283 |
| 2,818,069 | 8/1957 | Fenton | 128/283 |
| 2,971,510 | 11/1961 | Berger | 128/283 |
| 3,039,464 | 6/1962 | Galindo | 128/283 |
| 3,043,306 | 7/1962 | Hergatt et al. | 128/283 |
| 3,089,493 | 7/1963 | Galindo | 128/283 |
| 3,283,757 | 9/1966 | Nelsen | 128/283 |
| 3,339,546 | 10/1967 | Chen | 128/156 |
| 3,398,744 | 11/1968 | Hooper | 128/283 |
| 3,528,420 | 6/1970 | Nielsen | 128/283 |
| 3,557,790 | 5/1971 | Hauser | 128/283 |
| 3,661,153 | 1/1972 | Polk et al. | 128/275 |
| 3,736,934 | 5/1973 | Hennessy | 128/283 |
| 3,740,770 | 2/1973 | Villari | 128/295 |
| 3,759,415 | 9/1973 | Cloyd | 220/60 |
| 3,826,262 | 11/1974 | Blackwood | 128/283 |
| 3,827,435 | 3/1974 | Marsan | 128/285 |
| 3,906,951 | 2/1975 | Chen | 128/283 |
| 3,941,133 | 3/1976 | Chen | 128/283 |
| 3,970,085 | 7/1976 | Marsan | 128/283 |
| 4,046,408 | 9/1977 | Ausnit | 285/188 |

FOREIGN PATENT DOCUMENTS

| | | | |
|---|---|---|---|
| 219587 | 3/1957 | Australia . | |
| 491578 | 8/1976 | Australia . | |
| 143006 | 4/1971 | Czechoslovakia . | |
| 1105558 | 6/1961 | Fed. Rep. of Germany | 128/283 |
| 2347008 | 4/1975 | Fed. Rep. of Germany . | |
| 2453700 | 5/1976 | Fed. Rep. of Germany . | |
| 2316142 | 1/1977 | France . | |
| 351610 | 12/1972 | Sweden . | |
| 760939 | 1/1956 | United Kingdom . | |
| 751333 | 7/1956 | United Kingdom . | |
| 839818 | 12/1960 | United Kingdom . | |
| 1021145 | 1/1966 | United Kingdom . | |
| 1088992 | 3/1967 | United Kingdom . | |
| 1099455 | 5/1968 | United Kingdom . | |
| 1139715 | 9/1969 | United Kingdom . | |
| 1212904 | 1/1970 | United Kingdom . | |
| 1455784 | 3/1976 | United Kingdom . | |

Primary Examiner—C. Fred Rosenbaum
Assistant Examiner—T. J. Wallen
Attorney, Agent, or Firm—Lawrence S. Levinson; Stephen B. Davis

[57] ABSTRACT

A system is provided by which an ostomy bag can be securely coupled to an adhesive dressing that fits around the stoma and yet will permit the bag to be removed without disturbing the dressing. This system involves a first coupling member bonded to the dressing and a second coupling member bonded to the ostomy bag around the stomal opening. One coupling member consists of an upstanding rib or other projection which is dimensioned to sealingly engage an opening in the other coupling member.

29 Claims, 11 Drawing Figures

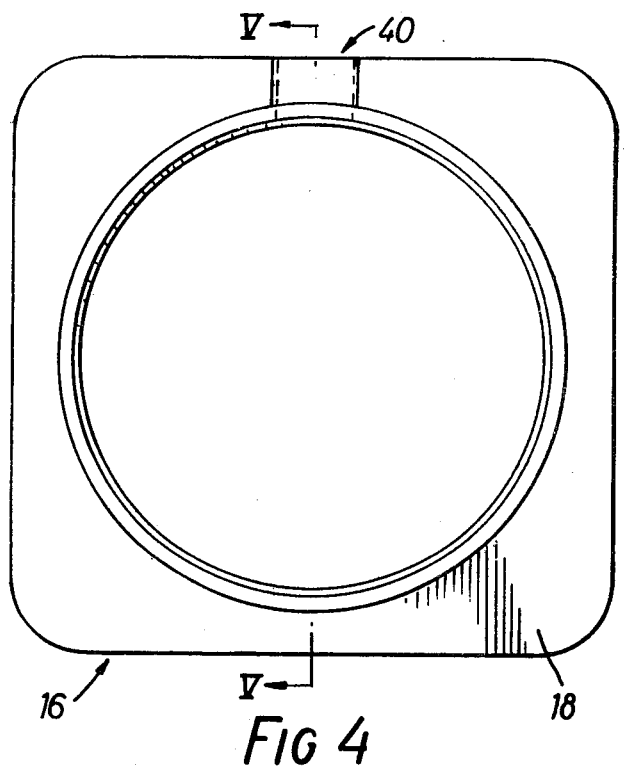
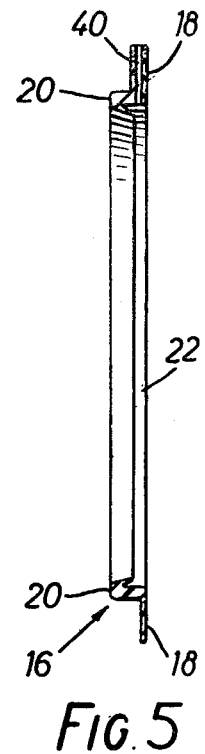
FIG 4    FIG.5
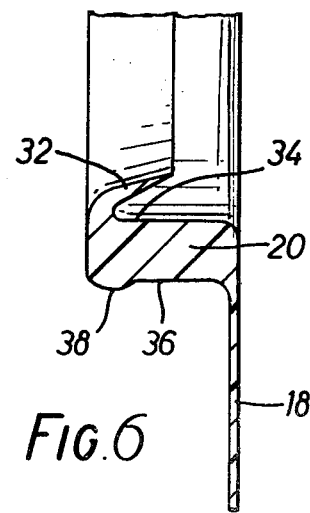
FIG.6

OSTOMY BAG

This is a continuation of application Ser. No. 881,274, filed Feb. 27, 1978, now abandoned.

BACKGROUND OF THE INVENTION

This invention relates to a coupling for joining an ostomy bag to a pad or surgical dressing. Ostomy bags are usually secured to a pad or surgical dressing which contacts the user's skin and surrounds the stoma. There is a need for a coupling between pad and bag which allows the bag to be readily removed when necessary, and replaced by a clean, empty bag. At the same time, it is essential that the coupling should be a secure one, and prevent leakage particularly of liquids and gases.

Efforts have been made, see for example the proposal in British Patent Specification No. 1,021,145 published in 1966, to provide a connector whereby the bag can be readily removed and replaced. But this arrangement involves two separate operations, firstly one must unscrew the connector which carries the bag from the connector which is secured to the body, and then one must unscrew the parts of the first connector in order to separate the bag therefrom. It will be appreciated that at this time the bag is full or partly-full of bodily waste products, and manipulation of the coupling will be an unpleasant operation even if, as is often not the case, the user has a high degree of dexterity.

British Patent Specification 1,099,455 discloses an application in which one ring co-operates with a second part-ring which is used to trap the neck of a bag when the two rings are interengaged with the bag mouth between them. If adequate security against leakage is to be provided, it is necessary that the two rings should be a tight fit; however this makes it difficult for the user to pull off the part-ring. As the part-ring is pulled off, there is the probability that the security of attachment of the first ring to the surgical dressing, or of the dressing to the skin of the wearer, will be impaired. This may also cause discomfort to the wearer.

In British Patent Specification No. 1,212,904, a complicated approach has been adopted. A clamping ring which has a ring-closing lever associated therewith embraces a mouth of a bag and causes the clamping ring to clamp the bag mouth to an annular shoulder of a member which is held against the user's body by a belt. Such a construction is relatively complicated and is not suitable for mass-production. In addition, removal of a full bag without spillage will require care and skill, and especially for old or infirm patients there is still an unsatisfied need, despite the many attempts shown in the patent literature, for a design which allows quick and easy bag-changing with reduced risk of spillage.

SUMMARY OF THE INVENTION

According to the invention, there is provided a coupling for joining a pad or dressing to an ostomy bag including a first member of closed loop form for defining a stoma aperture therein, the first member having a formation which defines two opposed walls, and a second member of closed loop form also defining a stoma aperture, the second member having a rib or projection dimensioned and positioned to be disposed between and to sealingly engage at least one of the walls when the members are connected.

The rib or projection may be gripped between the two walls of the second member in the mutually coupled positions of the members.

Preferably, one of the members is of channel form seen in cross-section and the other is dimensioned to be gripped between the mutually opposed channel walls.

The rib may, but need not necessarily have, a thin resilient deflectible seal strip extending therefrom which, when inserted in the channel, tends to spring outwardly to tightly engage one channel wall so improving the sealing properties of the coupling. The seal strip may be, but need not be, integral with the rib or projection.

The first and/or second coupling member may be secured to or integral with one or more outwardly extending ears. These may be provided for one or both of two purposes, namely to afford attachment points for a belt by which the user holds the bag on his body and to provide accessible parts which the user can grip with his thumb and a finger to pull apart the interengaged first and second members, when the bag is to be replaced.

The first and second coupling members are preferably, but need not necessarily be of circular form. A flange may extend from the rib all the way round its periphery, and may be located on the radially inner or radially outer surface of the rib. The first and second coupling members may but need not be of low density polyethlene. The first coupling member may have a rim extending towards the interior of the channel and located at or near the free end of one of the channel limbs. This improves the mechanical security of the coupling. The rim is preferably on the radially outer limb of the channel.

The first or the second coupling member may be made integral with the pad or secured to it, for example by an adhesive. In the case of a particularly advantageous form of the invention, the pad is made of a plastic adhesive material comprising a blend of a water-soluble or water-swellable hydrocolloid and a water-insoluble, viscous elastic binder. Such a material may be cast or formed in a mold to surround and thus form an article effectively integral with the first or second coupling member as the case may be. The other coupling member may be made effectively integral with the bag. For example, when both the bag and the coupling member are of synthetic plastics material, the two may be heat-welded together or secured together by an adhesive.

Either or both of the coupling members may be injection molded from any suitable synthetic plastics material.

The first or second coupling member may define a passageway leading from its interior to the exterior, and this passageway may contain a filter acting to reduce the odors in any gases which escape therethrough. The filter may be in the form of a replaceable cartridge containing carbon cloth.

It will be understood that the present invention extends to either of the coupling members as defined above if sold or offered for sale independently from the other. In particular the invention extends to a bag having one such coupling member (as broadly defined above); and it also extends to a pad having one such coupling member (as broadly defined above). It will be realized that one pad may last a given user several days, before it has to be replaced, whereas several bags are used per day. The invention is therefore not to be regarded as limited to the combination of a first and second coupling member.

BRIEF DESCRIPTION OF THE DRAWINGS

FIG. 4 is an elevation view of one form of second coupling member, looking towards the user;

FIG. 5 is a vertical axial section on the line V—V through the coupling member shown on FIG. 4;

FIG. 6 is an enlargement of part of FIG. 5;

FIG. 7 is an axial (or any radial) section through a modified first coupling member and FIG. 8 is a similar section through a complementary second coupling member;

DETAILED DESCRIPTION

Figure 1:
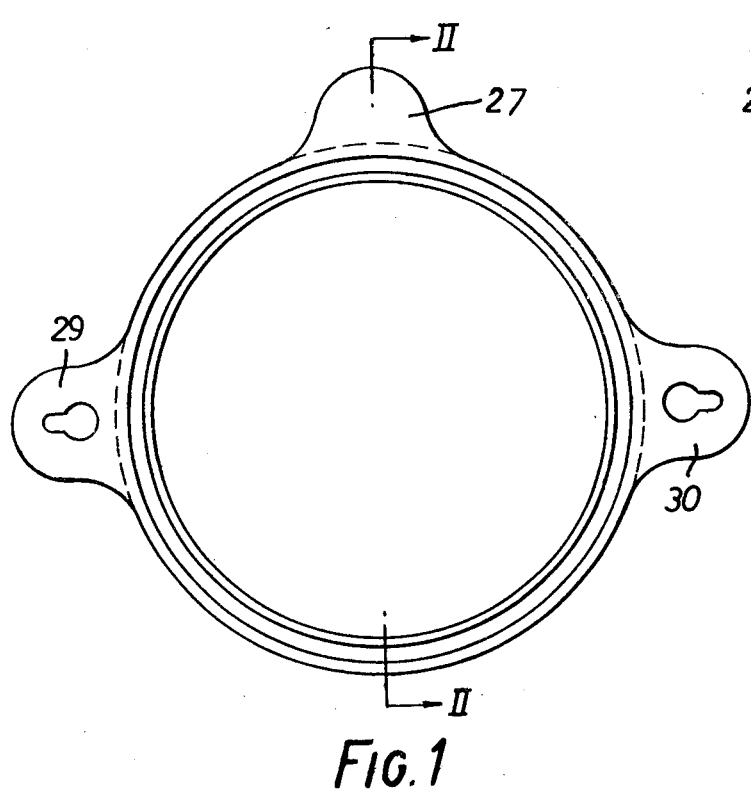
FIG. 1 is an elevation view of a first embodiment of the invention, illustrating a first coupling member, looking in a direction outwardly from the user.
Figure 2:
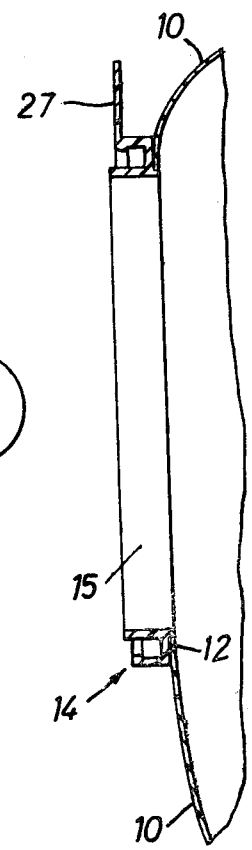
FIG. 2 is a vertical axial section on the line II—II through the coupling member shown in FIG. 1.
Figure 11:
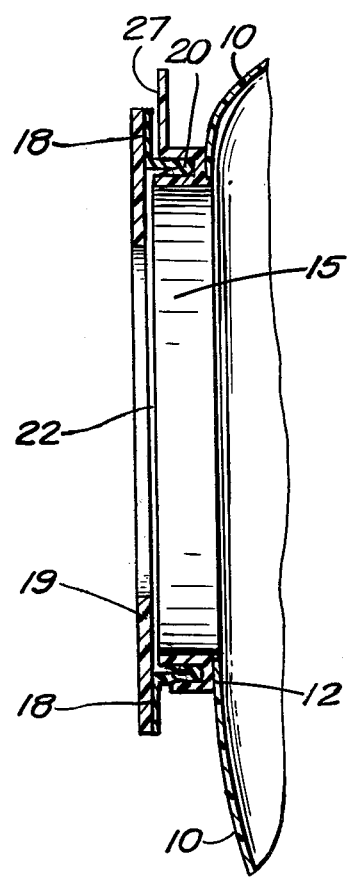
FIG. 11 is an axial section through the first embodiment of the invention (not showing passageway 40), showing the coupling members in the mutually coupled positions.

In FIGS. 1-6 the ostomy bag is indicated at 10, as note FIG. 2, and is secured by heat-welding to a surface 12, facing away from the user, on the first coupling member 14. This member is circular and defines an aperture 15 which in use surrounds the user's stoma. The aperture of course need not be circular but could be of any suitable shape. The second coupling member 16 (FIG. 5) is made of two parts, preferably integral with each other, namely a flange 18 and a circular rib or projection 20 which cooperates with the channel shaped first coupling member 14. The flange 18 has a circular aperture 22 and is intended to be secured to a pad or surgical dressing 19 as shown in FIG. 11 which has a similar circular aperture and whose opposite surface contacts the skin of the patient. The pad may be a dressing as disclosed and claimed in British Pat. No. 1,088,992.

Figure 3:
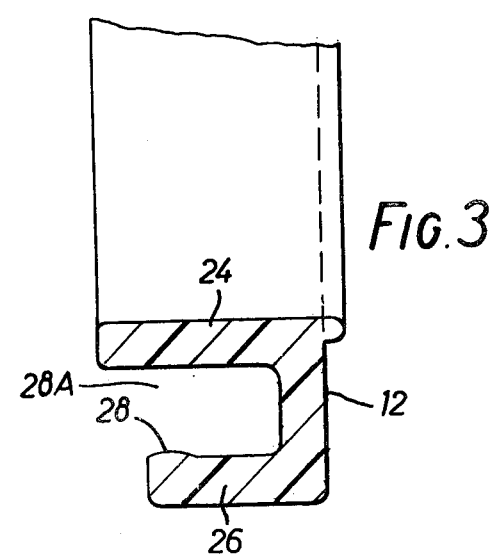
FIG. 3 is an elarged section taken in a vertical (or any radial) plane showing one form of rim construction on the member shown in FIGS. 1 and 2.

Referring to FIG. 3, the first coupling member 14 is of channel-shape seen in any radial cross-section and has a radially inner wall or limb 24 and a radially outer wall or limb 26. A rim 28 extends inwardly around the inner periphery of the wall 26 and, together with the wall 24, defines a restricted annular mouth or entry 28A into which, in use, the rib part 20 of the second coupling member 16 is pushed to firmly connect the first and second coupling members. Three ears 27, 29, and 30 (FIG. 1) are secured to or molded integrally with the channel and each may serve to be gripped and pulled by the user when he wishes to separate the bag 10 from the pad. The ears 29 and 30 also serve for attachment of a belt if desired. For convenience of the user, the ear 27 may be located at any position around the axis and need not be at "12 o'clock" as illustrated.

The second coupling member 16 (FIG. 6) is principally in the form of a cylindrical rib 20 extending substantially perpendicularly from the flat flange 18, and includes a thin resilient flexible and deflectible seal strip 32. As shown, this is of tapering form seen in cross-section and extends at an angle radially inwardly from an inner surface 34 of the rib. In use, when the two coupling members are engaged, it springs radially inwardly as shown in FIG. 11 to firmly engage the radially-inner wall 24 of the first coupling member to enhance the tight sealing properties of the coupling. Another surface 36 of the rib may be provided as shown with a peripheral rim 38 which cooperates with the rim 28 in providing mechanical security.

The seal strip 32 is illustrated as integral with the rib 20 but it could be a separate part adhesively or otherwise secured to the rib 20.

As seen in FIGS. 4 and 5, the second coupling member includes a passageway 40 by which gases can escape from the interior 22 of the coupling and hence from the interior of the bag when it is being worn by the user. The passageway 40 may contain filtering or deodorizing agents such as activated carbon, or fibrous active carbon cloth such as is described and claimed in British Pat. No. 1,301,101. The filter can be in the form of a replaceable cartridge housed within passageway 40 having one or more layers of carbon cloth arranged parallel to the path of the escaping gas. Rather than a single passageway, the cartridge can consist of a plurality of hollow pegs fixed into a holder located within passageway 40. Of course, other arrangements of vents and filters can be employed.

The arrangement illustrated in FIGS. 1 through 6 herein has the advantage of being light, inexpensive to manufacture, hygienic, secure and relatively easy to use.

Figure 7:
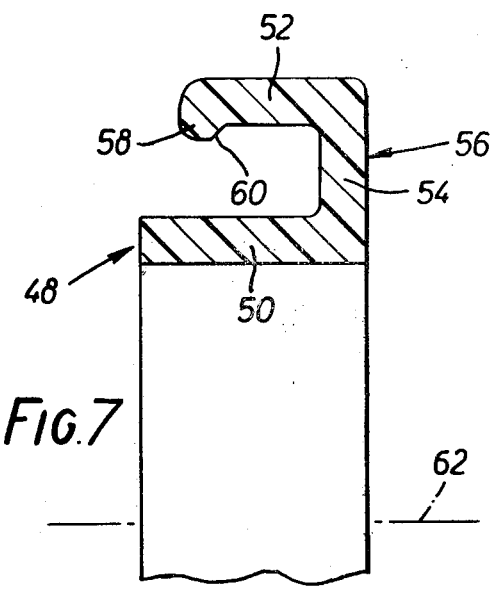
FIGS. 7 and 8 illustrate a second embodiment of the invention, which is a refinement of the embodiment shown in FIGS. 1-6.
Figure 8:
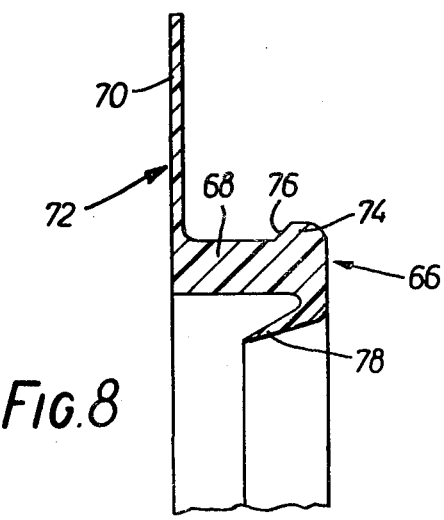

Referring now to FIGS. 7 and 8, in this version of the invention, the profile of the rim is chosen such that there is an annular surface inclined to the common axis of the coupling members and facing towards a diagonally opposite part of the channel section coupling member. The other coupling member, that is to say the rib of closed loop form, also has a rim extending towards the rim-carrying limb of the channel section coupling member. The rim on the rib preferably also has an inclined annular surface constructed to engage in face-to-face contact with the other annular surface when the two coupling members are in their mutually-coupled positions.

An important feature of the constructions so far described is that one coupling member has at least one pair of opposed walls between which a part of the other coupling member is trapped temporarily by the inherent resilience of the material, the latter being preferably low density polyethylene. A wide variety of profiles may be employed having this general characteristic.

The illustrated first coupling member 48 in FIG. 7 has radially inner and outer limbs 50 and 52 joined by a radially extending web 54. The outer limb 52 has a rim 58, and this has an annular surface 60 at approximately 45° to the axis 62 of the member 48. The ostomy bag (not shown) is secured by heat welding to surface 56 of first coupling member 48.

The second coupling member 66 seen in FIG. 8 is made of two parts, namely a rib 68 and an outwardly-extending flange 70. These are preferably but not necessarily integral. The second member may be molded as a single molding from synthetic plastics material such as low-density polyethylene. The pad or surgical dressing (not shown) which contacts the skin of the wearer is secured for example by heat welding or by adhesive to the surface 72 of the member 66. The rib 68 is of generally cylindrical form with a bead or rim 74 which has a flat annular surface 76 facing at an angle towards the flange 70. The surface 76 may be at about 45° to the axis of the coupling. A deflectible seal strip 78 engages the outer surface 55 of the inner wall 50 of the first coupling member 48.

The dimensions of the first and second coupling members, and in particular the width of the channel and the rib, the dimensions of the rim, and the material and dimensions of the peripheral seal strip 78 are all chosen to allow secure interconnection of the two coupling members in a gas-tight and liquid-tight manner, while allowing the user to manually separate the two members.

It will be appreciated that modifications are possible without departing from the invention. For example, the rim 58 could be placed on the radially inner wall 50 of the member 48, and the seal strip 78 and the rim 74 reversed in position on the member 66. Alternatively the ostomy bag could be secured to the coupling member 66 and the pad secured to the coupling member 48. As yet further alternatives, in any of the above constructions, the seal strip 78 could be separate or separable from its associated coupling member, and it could be disposed on either the radially inner or outer surface of the rib, or on the radially inner or outer limb of the channel section member. The seal strip can be omitted if the rib is a tight fit in the channel.

Figure 9:
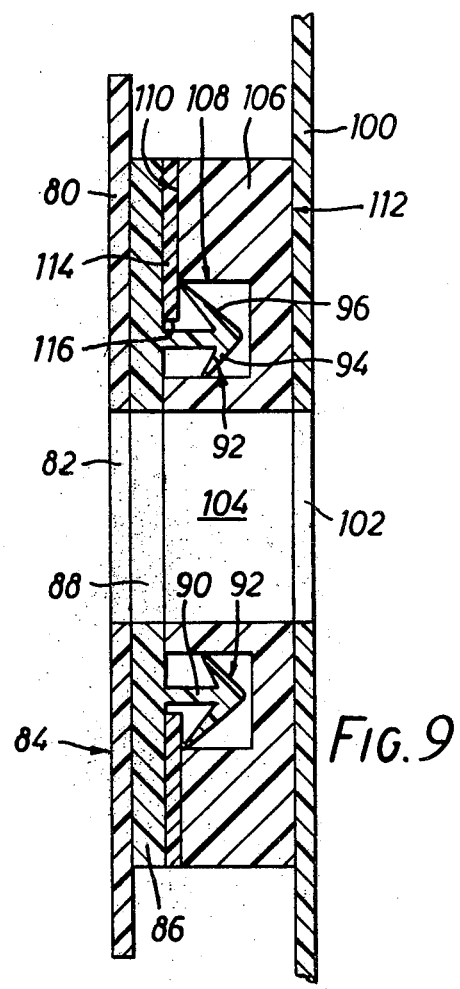
FIG. 9 is an axial section through a third embodiment of the invention, showing the coupling members in the mutually coupled positions but not showing the ostomy bag or the body of the wearer.

A third embodiment of the invention is illustrated in FIG. 9.

The first coupling member has a ring with an enlarged or arrowhead end which cooperates with a complementary annular recess in the second coupling member. The arrowhead end is push fit into the recess and is enabled to enter due to its shape and due to the inherent resilience of the material. It is trapped therein until a substantial separating force is applied.

FIG. 9 shows a pad 80 of the surgical material such as that disclosed and claimed in British Pat. No. 1,088,992. The pad has a central aperture 82 and its surface 84 is adhesive to the body of the user. The stoma of the user projects outwardly through the aperture 82. The pad is fixed in any convenient way (e.g. adhesive, heat welding) to a flat plate or disc 86 which has a central aperture 88 in approximate registry with the aperture 82. The disc 86 has integral therewith, or secured thereto, a ring 90 which encircles the aperture 88 and extends away from the disc 86 in an axial direction, that is, away from the user's body. The ring 90 has an enlarged and resilient end portion 92 which in the preferred embodiment of this version of the invention is of arrowhead configuration, consisting of two flanges 94 and 96. The parts 86, 90, 92, 94, 96 constitute a first coupling member.

A second coupling member is shown attached to an ostomy bag. One wall (the body side wall) 100 of the bag is shown having an aperture 102 in approximate registry with an aperture 104 in a ring 106. The ring 106 has an annular channel 108 let into its surface 110. The opposite surface 112 of the ring 106 is attached (e.g. by adhesive or welding) to the bag wall 100. The ring 106 constitutes one part of the second coupling member and a second part thereof is formed by an apertured disc 114. This is fixed to the surface 110 e.g. by heat welding or by suitable adhesive. The radially inner wall 116 of the disc 114 is located a distance from the axis which is greater than the radially inner wall of the channel 108 and less than the radially outer wall thereof. In other words, the disc 114 partly overlaps the channel and defines a restricted entry thereto, through which the resilient end portion 92 of the first coupling member can be manually forced to temporarily but securely connect the two coupling members together. That is to say, in this way while the pad 80 stays attached to the user, he or she can readily remove the ostomy bag 100 and replace it with a clean, fresh one.

It will be seen that the two coupling members are all of a simple shape and construction, and can be readily and inexpensively manufactured from synthetic plastics material using only simple molds and straight forward, trouble-free procedures.

While an arrowhead configuration 92 is preferred, it will be appreciated that other configurations (e.g. a bull head) could be used without sacrificing the advantages.

Figure 10:
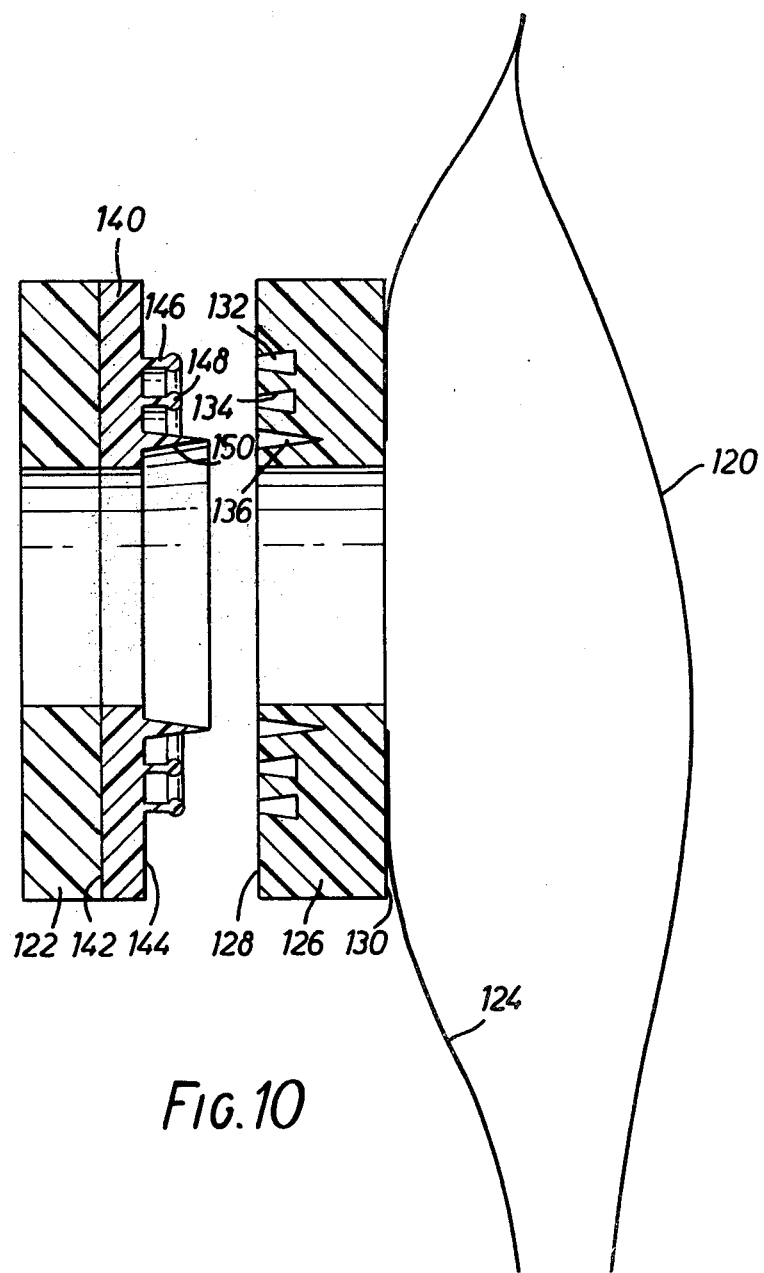
FIG. 10 is an axial section through a fourth embodiment of the invention showing a stud and socket engagement between the first and second coupling members.

FIG. 10 illustrates a fourth embodiment of the invention. This embodiment of the invention includes two coupling members, one for attachment to a pad or dressing and one to an ostomy bag. A stud and socket type of connection is employed. One member has a formation which defines two opposed annular walls, and the other coupling has a formation which defines an annular projection of a size and configuration chosen to be gripped between the opposed walls of the first coupling when the two coupling members are connected.

In such an arrangement, the direction of relative movement between the two coupling members is generally axial, that is, towards and away from the abdomen of the user, and the annular projection is positioned to project from one of the coupling members in a generally axial direction towards the other coupling member.

As disclosed herein, a coupling of the kind aforesaid comprises a first and a second coupling member which are manually separable, the first member having a body with a central aperture and a pair of generally concentric annular grooves of re-entrant cross-section, and the second member also having a body with a central aperture and having a complementary pair of ribs upstanding therefrom, the free ends of the ribs being enlarged relative to the remainder of the respective ribs so that the two coupling members can be joined by manually forcing the enlarged ends of the ribs into the respective grooves. It will be understood that the first and second coupling members are of a resilient material, such as synthetic plastics material, which is easily deformed under manually applied pressure.

Either the first or the second member may have a sealing wall extending around its aperture and this, when the two members are coupled, extends into a complementary groove or recess in the other coupling member to provide a liquid-tight and gas-tight seal between the coupling members. In this way, undesired escape of unpleasant odors or liquids can be achieved even though the ostomy bag and the coupling member to which it is fixed can be readily removed and replaced with a clean one by its wearer, with small danger of spillage.

The first coupling member may be fixed to the pad and the second to the bag, or vice versa. The sealing wall may be on the first member and the groove or recess (which is additional to the pair of re-entrant grooves) may be on the second coupling member, or vice versa.

The sealing wall may be radially inwardly or outwardly of the pair of re-entrant grooves, or it may be located between them, viewed in a radial direction.

As stated, FIG. 10 is a diagramatic axial cross-section through a coupling showing the two coupling members separated from one another, the first being connected to an ostomy bag and the second being connected to a surgical dressing pad. The latter is preferably a dressing as disclosed and claimed in British Pat. No 1,088,992.

The illustrated coupling is between a bag 120 and a pad 122. The bag has an orifice in its wall 124. The latter is secured to a first coupling member 126 in the form of a resilient synthetic plastics ring having generally flat faces 128 and 130. The face 128 of the ring 126 has a concentric pair of re-entrant grooves 132, 134 and an annular recess 136 of V-shaped cross-section.

The second coupling member is also of resilient synthetic plastics material and is in the form of a flat ring 140 having a face 142 to which is secured the surgical dressing pad 122. The other face 144 has a pair of ribs 146, 148 and a sealing wall 150 projection from it, and each rib has an enlarged head end which is slightly wider than the entry to its associated re-entrant groove.

It will be understood that with this construction, the two coupling members can be securely but temporarily joined by manually pushing them together so that the heads of the ribs 146 and 148 are received in the respective re-entrant grooves 132 and 134, and the sealing wall is received in its recess 136. Preferably, the dimensions of the parts are such that when coupled, the faces 128 and 144 come into mutual contact. In the drawing, the axial extents of the parts 146, 148 and 150 have been exaggerated for clarity of illustration.

What is claimed is:

1. An ostomy appliance having an ostomy bag provided with a stoma encircling opening adjacent one end of one side thereof, a coupling member having a portion secured to said one end of said ostomy bag around said bag opening, said portion extending outwardly from said side of said ostomy bag, said portion having a passage extending between the free end of said coupling member and its end contiguous to said ostomy bag providing an opening of substantially the same size as said ostomy bag opening whereby a stoma may extend into said passage and said ostomy bag, said portion having an uninterrupted surface exposed to said passage and to the interior of said ostomy bag whereby the accumulation of soil on and around said coupling is minimized, said portion having a first engaging element formed thereon dimensioned to engage securely with a second engaging element on a coupling member secured to the body.

2. The ostomy appliance of claim 1 wherein said first engaging element is constituted by a channel formed on said portion outwardly of said passage to receive a second engaging element constituted by a projection extending from a coupling member secured to the body and wherein said channel is dimensioned to engage the projection to hold the projection securely therein.

3. The ostomy appliance of claim 1 wherein said first engaging element is constituted by a projection formed on said coupling member extending away from said ostomy bag to engage a second engaging element constituted by a channel formed on a coupling member secured to the body and wherein said projection is dimensioned to engage securely in the channel.

4. The ostomy appliance of claims 2 or 3 wherein said first and second engaging elements are formed outwardly of said passage and completely encompass it.

5. The ostomy appliance of claims 2 or 3 wherein said projection has a thin resilient deflectible seal strip extending therefrom sealingly engaging a side of said channel when said first and second engaging elements are engaged with each other.

6. An ostomy appliance as set forth in claim 4 wherein said projection has a thin resilient deflectible sealing strip extending therefrom completely around its outer periphery to sealingly engage a side of said channel when said first and second engaging elements are engaging each other.

7. An ostomy appliance as set forth in claim 6 wherein said first engaging element is provided with ears extending radially outwardly therefrom.

8. An ostomy appliance as set forth in claim 7 wherein said coupling member is made of low density polyethylene.

9. An ostomy appliance comprising a pad or dressing having a generally circular aperture for passage of the stoma, said pad or dressing aperture encircled by a coupling member and an ostomy bag also having a generally circular aperture for passage of the stoma, said bag aperture encircled by a second coupling member, one of said coupling members being two opposed walls of closed loop annular channel form and the other coupling member of closed loop form having a rib or projection dimensioned to be gripped between the mutually opposed channel walls when said coupling members are connected, said rib or projecton having a thin resilient deflectible seal strip extending therefrom, which, when said rib or projection is disposed between said walls, springs away therefrom to sealingly engage one of said walls, and in which each coupling member is formed of resilient synthetic plastics materials.

10. An appliance according to claim 9 in which said coupling member of channel form is attached to said bag and said other coupling member having a rib or projection is attached to said pad or dressing.

11. An appliance according to claim 9 in which said coupling member of channel form is attached to said pad or dressing and said other coupling member having a rib or projection is attached to said bag.

12. An appliance according to claim 9 in which said rib or projection has a peripheral bead extending therefrom in a direction opposite said deflectible seal strip and one of said channel walls has a complementary bead positioned to improve the mechanical security of the coupling.

13. An appliance according to claim 12 in which each of said two beads has an annular surface thereon inclined to the common axis of said coupling members when connected, the arrangement being such that said two annular surfaces are in face-to-face contact when said two members are in their mutually coupled positions.

14. An appliance according to claim 13 in which said coupling member of channel form is attached to said bag and said other coupling member having a rib or projection is attached to said pad or dressing.

15. An appliance according to claim 13 in which said coupling member of channel form is attached to said pad or dressing and said other coupling member having a rib or projection is attached to said bag.

16. An appliance according to claim 9 in which the one of said coupling members that is secured to the bag has one or more radially outwardly extending ears.

17. An appliance according to claim 9 in which one or both of said coupling members is made of low density polyethylene.

18. An appliance according to claim 9 in which said pad or dressing is made of a plastic adhesive material comprising a blend of a water-soluble or water-swellable hydrocolloid and a water-insoluble, viscous elastic binder.

19. An appliance according to claim 9 in which one of said coupling members defines a gas exit passageway leading from the aperture to the exterior.

20. An appliance according to claim 19 in which said gas exit passageway contains a filter.

21. An appliance according to claim 20 in which said filter is in the form of a replaceable filter cartridge.

22. An appliance according to claim 21 in which said cartridge comprises a housing having an inlet and an outlet and at least one layer of carbon cloth disposed therein so that the gas in passing from said housing inlet to the outlet passes parallel to the surface of said layer of carbon cloth.

23. An appliance according to claim 22 in which said housing has a plurality of hollow pegs at one of its ends by which it is fixed into a holder located in said gas exit passageway, the interior of said pegs serving as the inlet.

24. An ostomy appliance comprising a pad or dressing having a generally circular aperture for passage of the stoma, said pad or dressing aperture encircled by a coupling member and an ostomy bag also having a generally circular aperture for passage of the stoma, said bag aperture encircled by a second coupling member, one of said coupling members being two opposed walls of closed looped annular channel form and the other coupling member having a rib or projection dimensioned to be gripped between the mutually opposed channel walls when said coupling members are connected, one of said walls having a thin resilient deflectible seal strip extending therefrom which, when said rib or projection is inserted between said walls, springs outwardly to engage said rib or projection, and in which each coupling member is formed of resilient synthetic plastics material.

25. An appliance according to claim 24 in which said coupling member of channel form is attached to said bag and said other coupling member having a rib or projection is attached to said pad or dressing.

26. An appliance according to claim 24 in which said coupling member of channel form is attached to said pad or dressing and said other coupling member having a rib or projection is attached to said bag.

27. An ostomy appliance comprising a pad or dressing having a body contacting surface and an outer surface with an aperture for passage of the stoma extending through said pad or dressing, a coupling member extending outwardly from said pad or dressing and encircling the intersection of said aperture and the outer surface of said pad or dressing and an ostomy bag also having an aperture in one bag wall for passage of the stoma with a second coupling member affixed to said bag wall around the periphery of said bag wall aperture and extending outwardly from said bag wall, said bag coupling member being two opposed walls of closed loop channel form and said pad or dressing coupling member being a closed loop form having a rib or projection dimensioned to be gripped between the opposed channel walls when said coupling members are connected, and a thin resilient seal strip extending at an angle radially inward from an inner surface of said rib or projection which engages the outer surface of said inner channel wall and wherein said rib or projection has a peripheral bead extending therefrom in a direction opposite said deflectible seal strip and said outer channel wall has a complementary bead on its inner surface, each of said two beads having an annular surface inclined to the common axis of said coupling members when connected, the arrangement being such that said two annular surfaces are in face-to-face contact when said two members are in their mutually coupled positions.

28. An appliance of claim 27 wherein each coupling member is of resilient synthetic plastics material and said pad or dressing is made of a plastic adhesive material comprising a blend of a water-soluble or water-swellable hydrocolloid and a water-insoluble viscous elastic binder.

29. An appliance of claim 28 wherein said bag coupling member has one or more radially outwardly extending ears.

* * * * *

UNITED STATES PATENT OFFICE
CERTIFICATE OF CORRECTION

PATENT NO. : 4,460,363
DATED : July 17, 1984
INVENTOR(S) : Peter L. Steer, John V. Edwards It is certified that error appears in the above-identified patent and that said Letters Patent are hereby corrected as shown below:

Col. 8, line 47 "An" should be -- The -- .
Col. 10, line 38 "An" should be -- The -- .
Col. 10, line 44 "An" should be -- The -- .

Signed and Sealed this

Twenty-third Day of October 1984

[SEAL]

Attest:

GERALD J. MOSSINGHOFF

Attesting Officer     Commissioner of Patents and Trademarks

UNITED STATES PATENT AND TRADEMARK OFFICE
CERTIFICATE OF CORRECTION

PATENT NO. : 4,460,363
DATED : July 17, 1984
INVENTOR(S) : Peter L. Steer, John V. Edwards It is certified that error appears in the above-identified patent and that said Letters Patent are hereby corrected as shown below:

On the title page insert:

[30] Foreign Application Priority Data
March 30,1977 [GB] United Kingdom   13411/77
November 17,1977 [GB] United Kingdom   47927/77
November 17,1977 [GB] United Kingdom   47928/77
November 17,1977 [GB] United Kingdom   47930/77
January 27,1978 [GB] United Kingdom   13411/77

Signed and Sealed this

Twenty-second Day of October 1985

[SEAL]

Attest:

DONALD J. QUIGG

Attesting Officer

Commissioner of Patents and
Trademarks—Designate